(12) United States Patent
Vegar et al.

(10) Patent No.: US 12,145,048 B2
(45) Date of Patent: Nov. 19, 2024

(54) PROCESSING OF DATA COLLECTED VIA AN INSTRUMENTED MOUTHGAURD DEVICE, INCLUDING IDENTIFICATION OF FALSE IMPACTS

(71) Applicant: HitIQ Limited, South Melbourne (AU)

(72) Inventors: Michael Vegar, Queenscliff (AU); Ben Nizette, Queenscliff (AU); David Erikson, Queenscliff (AU)

(73) Assignee: HitIQ Limited, South Melbourne (AU)

( * ) Notice: Subject to any disclaimer, the term of this patent is extended or adjusted under 35 U.S.C. 154(b) by 338 days.

(21) Appl. No.: 17/653,356

(22) Filed: Mar. 3, 2022

(65) Prior Publication Data

US 2022/0280859 A1 Sep. 8, 2022

(30) Foreign Application Priority Data

Mar. 3, 2021 (AU) ................................ 2021900594

(51) Int. Cl.
*A63B 71/00* (2006.01)
*A61B 5/00* (2006.01)
*A63B 71/08* (2006.01)

(52) U.S. Cl.
CPC ............ *A63B 71/085* (2013.01); *A61B 5/682* (2013.01); *A61B 2503/10* (2013.01); *A61B 2562/0219* (2013.01); *A63B 2220/40* (2013.01); *A63B 2220/53* (2013.01); *A63B 2220/58* (2013.01); *A63B 2220/803* (2013.01); *A63B 2225/50* (2013.01)

(58) Field of Classification Search
CPC ........ A61B 2562/0219; A61B 2503/10; A63B 2220/40; A63B 2220/53; A63B 2220/58; A63B 2220/803; A63B 2225/50
See application file for complete search history.

(56) References Cited

U.S. PATENT DOCUMENTS

| | | | |
|---|---|---|---|
| 2014/0188010 A1* | 7/2014 | Paris | A61B 5/682 600/595 |
| 2017/0071526 A1* | 3/2017 | Lyren | A63B 71/085 |
| 2017/0156635 A1* | 6/2017 | Kuo | A61B 5/682 |
| 2018/0154242 A1 | 6/2018 | Austin et al. | |
| 2018/0196079 A1 | 7/2018 | Austin et al. | |

FOREIGN PATENT DOCUMENTS

| | | | | |
|---|---|---|---|---|
| AU | 2020900733 | | 3/2020 | |
| AU | 2020904214 | | 11/2020 | |
| CN | 107530155 | A * | 1/2018 | ............... A61C 7/08 |
| CN | 111330163 | A * | 6/2020 | ........... A61C 19/006 |
| EP | 3329844 | A1 * | 6/2018 | ........... A61B 5/1122 |
| WO | WO-2017091708 | A2 * | 6/2017 | |
| WO | WO-2020123875 | A1 * | 6/2020 | ........... A61B 5/0002 |

* cited by examiner

*Primary Examiner* — Jamel E Williams
(74) *Attorney, Agent, or Firm* — TraskBritt

(57) ABSTRACT

The present disclosure relates to technology adapted for improved assessment of brain injuries in a human subject. For example, in some embodiments the invention relates to improved processing of data collected via an instrumented mouthguard device, including identification of false impacts. It will be appreciated that the invention is not limited to such a field of use, and is applicable in broader contexts. For example, the technology may be applied to detect other changes in physical performance, beyond head injuries. Furthermore, the technology may be applied in respect of other wearable devices which detect/measure head impacts, for example helmets.

38 Claims, 7 Drawing Sheets

PROCESSING OF DATA COLLECTED VIA AN INSTRUMENTED MOUTHGAURD DEVICE, INCLUDING IDENTIFICATION OF FALSE IMPACTS

CROSS-REFERENCE TO RELATED APPLICATION

Pursuant to 35 U.S.C. § 119(a), this application claims the benefit of the filing date of Australian Patent Application Serial No. AU 2021900594, filed Mar. 3, 2021, for "Improved Processing of Data Collected Via an Instrumented Mouthguard Device, Including Identification of False Impacts," the disclosure of which is hereby incorporated herein in its entirety by this reference.

TECHNICAL FIELD

The present invention relates, in various embodiments, to technology adapted for improved assessment of brain injuries in a human subject. For example, in some embodiments, the invention relates to improved processing of data collected via an instrumented mouthguard device, including identification of false impacts. While some embodiments will be described herein with particular reference to those applications, it will be appreciated that the invention is not limited to such a field of use, and is applicable in broader contexts. For example, the technology may be applied to detect other changes in physical performance, beyond head injuries. Furthermore, the technology may be applied in respect of other wearable devices which detect/measure head impacts, for example, helmets.

BACKGROUND

Any discussion of the background art throughout the specification should in no way be considered as an admission that such art is widely known or forms part of common general knowledge in the field.

Brain injuries, particularly those sustained during participation in contact sports, are becoming an increasingly important focus of attention. For example, head impacts sustained during sport can have serious effects of both short term and long-term participant welfare. For example, it is valuable to better understand the nature of a suspected brain injury in terms of: (i) whether a participant should be rested from participation; (ii) an extent to which the injury should prevent a return to activity; (iii) a degree of seriousness of an injury, for instance insofar as that might affect treatment and management; and (iv) better understanding cumulative effects of successive brain injuries for a given participant.

With this in mind, various forms of head impact sensors have been developed, including sensor-fitted helmets, and instrumented mouthguards. In relation to the latter, whilst there has been a significant amount of research and development into hardware and processing techniques, the ability of instrumented mouthguards to accurately detect impacts suffers from limitations, including as a result of spikes in accelerometer data which are due to factors other than head impacts. This may include direct impacts, out-of-mouth events, and the like.

BRIEF SUMMARY

It is an object of the present invention to overcome or ameliorate at least one of the disadvantages of the prior art, or to provide a useful alternative.

Example embodiments are described below in the section entitled "claims."

Reference throughout this specification to "one embodiment," "some embodiments" or "an embodiment" means that a particular feature, structure or characteristic described in connection with the embodiment is included in at least one embodiment of the present invention. Thus, appearances of the phrases "in one embodiment," "in some embodiments" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

As used herein, unless otherwise specified the use of the ordinal adjectives "first," "second," "third," etc., to describe a common object, merely indicate that different instances of like objects are being referred to, and are not intended to imply that the objects so described must be in a given sequence, either temporally, spatially, in ranking, or in any other manner.

In the claims below and the description herein, any one of the terms comprising, comprised of or which comprises is an open term that means including at least the elements/features that follow, but not excluding others. Thus, the term comprising, when used in the claims, should not be interpreted as being limitative to the means or elements or steps listed thereafter. For example, the scope of the expression a device comprising A and B should not be limited to devices consisting only of elements A and B. Any one of the terms including or which includes or that includes as used herein is also an open term that also means including at least the elements/features that follow the term, but not excluding others. Thus, including is synonymous with and means comprising.

As used herein, the term "exemplary" is used in the sense of providing examples, as opposed to indicating quality. That is, an "exemplary embodiment" is an embodiment provided as an example, as opposed to necessarily being an embodiment of exemplary quality.

BRIEF DESCRIPTION OF THE DRAWINGS

Embodiments of the invention will now be described, by way of example only, with reference to the accompanying drawings in which.

DETAILED DESCRIPTION

Figure 1A:
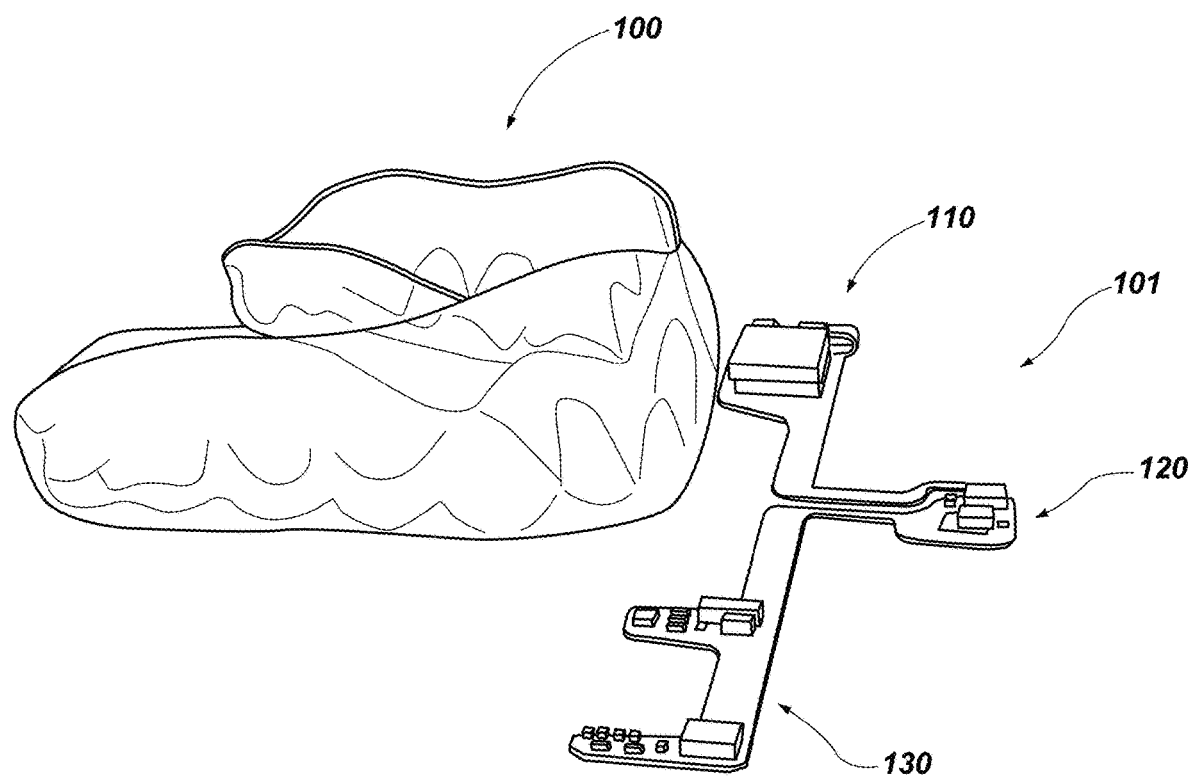
FIG. 1A to FIG. 1D illustrate an instrumented mouthguard in varying states of assembly.
Figure 1B:
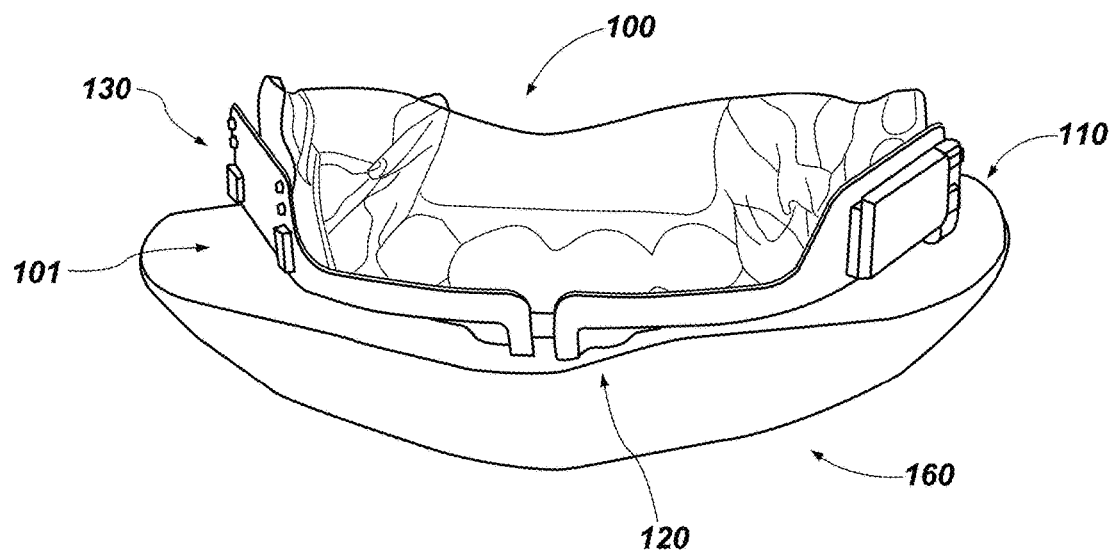
Figure 1C:
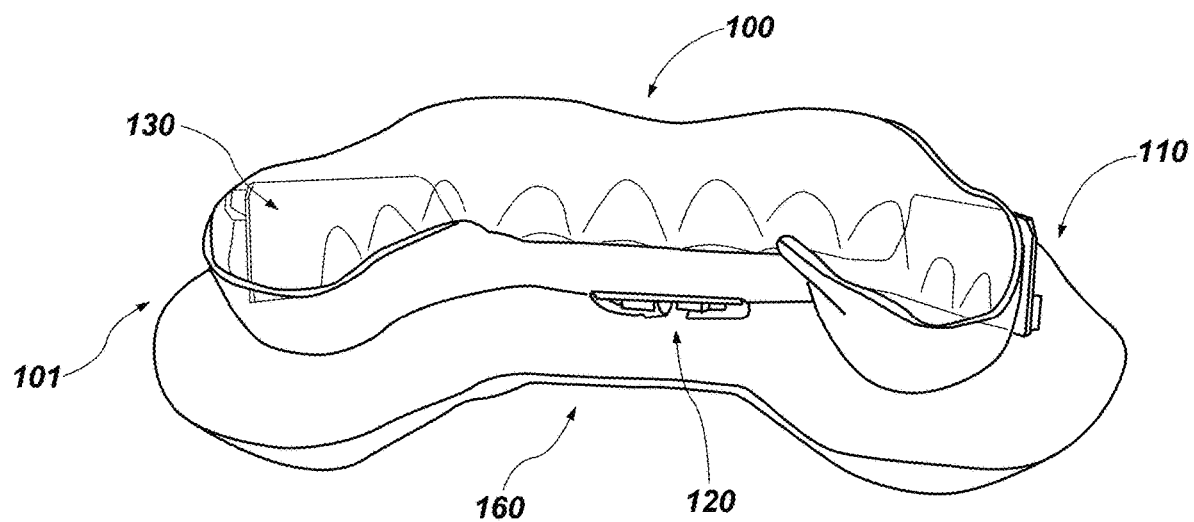
Figure 1D:
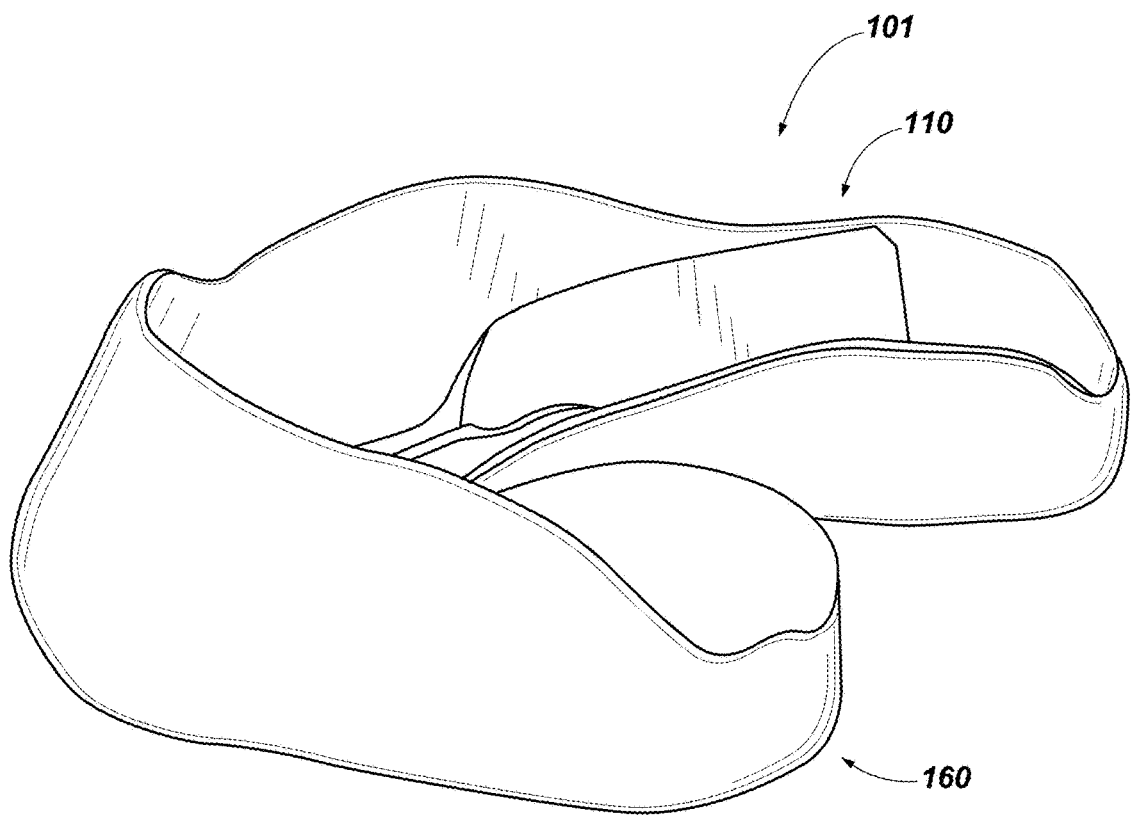

The present invention relates, in various embodiments, to improved processing of data collected by an instrumented mouthguard device. Specifically, this processing relates to a scenario where a subject wears an instrumented mouthguard device, which includes a plurality of motion sensing components, and data from those motion sensing components is processed thereby to derive impact parameters for an impact event. In some embodiments, the impact parameters include acceleration metrics associated with the impact event, and/or a dosage signal which is fed to a model, for example, a finite element analysis model, thereby to model effect of the impact on the subject's brain.

Embodiments have been primarily directed to enable improved determination of impact parameters, particularly in situations where instrumented mouthguard sensor component data is affected by deformation of a mouthguard body (which is formed from deformable plastic material). For example, such deformation may occur in the following scenarios:

(i) In the case of a direct impact to a subject's face. For example, this is especially relevant in sports such as boxing and MMA, where it is expected that participants may receive direct impacts to the mouth/jaw area. Such impacts also occur in a range of other contact sports, including various codes of football and rugby.

(ii) In the case that the mouthguard is not contained in the subject's mouth. For example, the mouthguard may be dropped, carried in a pocket, and so on, and at such times deliver false data representative of predicted head impacts.

It will be appreciated that technology disclosed herein is not only adapted to improve instrumented mouthguard data processing in either or both of these scenarios, but also in other situations. For example, this may include situations where a given motion sensing component has become damaged and/or faulty (it will be appreciated that the human mouth is a relatively hostile environment in which to contain sensitive electronic components).

A preferred embodiment provides a method for processing impact event data for an impact event, wherein the impact event data is derived from an instrumented mouthguard device, wherein the instrumented mouthguard device includes: a body formed of deformable materials, wherein the body is shaped to be worn by a subject as a mouthguard; and motion sensing components including a plurality of spaced apart accelerometers and at least one gyroscope. The method includes determining a measurement of acceleration at a specified location on the subject's head using a subset of the motion sensing components, thereby to account for localized deformation of the body proximal a given one of the motion sensing components.

In broad terms, the technology disclosed involves a combination of two main elements. Firstly, an instrumented mouthguard is manufactured having sufficient motion sensor components to allow reliable solutions to a rigid body kinematics problem with a reduced subset of those motion sensor components. Secondly, processing techniques are performed based on a rigid body assumption, whereby the human head is assumed to be a rigid body, and spaced apart motion sensor components within the instrumented mouthguard are expected to move correspondingly as though effectively mounted to a rigid body.

In a preferred embodiment, an instrumented mouthguard device includes the following components:

Three 3-axis accelerometers, at spaced apart locations on the mouthguard body, referred to as "component zones." A mouthguard calibration process is preformed thereby to determine relative locations and orientations of these accelerometers, and preferably a spatial relationship between those and a center of gravity of the human head. For example, such calibration may be performed as described in Australian Provisional Patent Application 2020900733, which is incorporated by cross reference. In overview, this may include a process whereby data samples are collected during spinning of the guard in various controlled orientations.

A gyroscope, which is optionally located proximal one of the gyroscopes in one of the component zones. This is also in some embodiments calibrated for position and/or orientation.

For the present purposes, it is assumed that the component zones include a frontal zone (for example, behind front teeth) and left/right side zones (for example, adjacent molars). The gyroscope is provided in the frontal zone (although in further embodiments, it may be provided elsewhere).

Samples from the accelerometer and gyroscope are used as input to a model, thereby to calculate acceleration at the center of gravity of the subject's head during mouthguard usage, for example, to analyze head impacts. The presence of three accelerometers and a gyroscope allows for this acceleration problem to be solved in a plurality of ways. For example, the model involves solving a differential equation with multiple inputs, and the available inputs exceed what is required for the equation to be solved. In particular, center of gravity acceleration may be determined in any of the following ways:

Using all three accelerometers, plus the gyroscope.
Using two of the accelerometers, plus the gyroscope.
Using three of the accelerometers, without the gyroscope (in which case the three accelerometers in combination are used to provide an equivalent of gyroscope data).

Which of these produces a most accurate result will depend on the nature of an impact. In particular, if an impact involves a strike adjacent one of the component zones, that may cause deformation on the jaw, and hence movement in that component zone which violates a rigid body assumption. Accordingly, in the case of a direct impact to the side of a subject's jaw, it is more accurate to use two accelerometers (from component zones away from the strike) plus the gyroscope.

It is also possible, although more challenging, to use two accelerometers and no gyroscope. For example, this may be achieved using a particle filter. This may be useful where a frontal impact has rendered data from both the frontal component zone accelerometer and gyroscope problematic.

In some embodiments, multiple input combinations are tested and results compared. For example, this may allow for verification of gyroscope data accuracy. For example, a technique includes comparing one or more acceleration results determined using the gyroscope with one or more determined without the gyroscope (and/or comparing a gyroscope value inferred from the three accelerometers with the physical gyroscope value).

Preferred embodiments provide methods for processing impact event data for an impact event, wherein the impact event data is derived from an instrumented mouthguard device. For the purposes of these embodiments, the instrumented mouthguard device includes:

A body formed of deformable materials, wherein the body is shaped to be worn by a subject as a mouthguard. Examples below focus primarily on implementations wherein the body is uniquely customized for a specific subject.

A plurality of component zones embedded in the body, wherein the component zones are spaced apart, and wherein each component zone includes one or more motion sensor components. The term "motion sensor component" includes, by way of example, an accelerometer (such as a 3-axis accelerometer) and a gyroscope.

The term "impact event" refers to a period of time during which a head impact affecting the subject is predicted to have occurred, based on data from one or more of the motion sensor components. For example, this may be defined by a period of time during which acceleration readings from one or more of the motion sensor components are above a threshold value. An impact event is "predicted" to have occurred, on the basis that the sensor data may result from mouthguard activity other than a head impact.

The methods include:
(i) Determining that the impact event data from a given one of the motion sensor components is affected by local deformation of the mouthguard body. For example, this may be determined based on comparative processing of data from the individual motion sensor components which reveals deviation from a rigid body assumption. That is, when data collected at individual spaced apart motion sensor components is transformed to a common positional frame of reference (for example, the center of gravity of the subject's head), there should be a threshold level of consistency between measurements. However, if that level of threshold consistency is not met, this likely indicates that the mouthguard has not behaved as a rigid body, and has deformed over the course of an impact event. Such data artefacts may present themselves as asymmetries in acceleration values.
(ii) Determining impact parameters for the impact event which account for that local deformation of the mouthguard body. Examples are discussed further below. In overview, two main approaches include: (A) exclusion of data from a given motion sensor component when calculating impact parameters; or (B) determining that the impact data is invalid, for example, as an "out-of-mouth" impact (the mouthguard was not in the subject's mouth when the impact data was recorded). The latter may be applied where deviation from the rigid body assumption exceeds a predefined threshold.

The term "impact parameters" should be read to cover a range of potential parameters, which are calculated from motion sensor component data. These may include values relating to linear and/or rotational accelerations, peak linear and/or rotational accelerations, dosage signals configured to be provided as input for computer models (for example, a finite element analysis model) and so on. The impact parameters are preferably determined for a predefined common location on the subject's head, for example, an approximated center of gravity. This may be achieved by applying transforms to vectors provided by motion sensor components at their respective locations. Example technology for establishing such transforms is discussed in Australian Provisional Patent Application 2020900733, which is herein incorporated by cross reference.

Examples are described in more detail below by reference to an example instrumented mouthguard device which collects redundant data for impact events. The term "redundant data" refers to having motion sensor data which is not necessary to reliably determine acceleration parameters for the center of gravity of the subject's head. That is, where a minimalist processing model requires N motion sensor components to solve for center of gravity acceleration, the instrumented mouthguard provides N+X motion sensor components, where X is an integer≥1. There may be multiple available processing models, each requiring input from N+Y motion sensor components where Y is an integer≥0 (and usually ≤X). In some embodiments, a processing technique includes executing a given processing model using multiple combinations of sensor subsets. Such an approach allows for determination and/or selection of a result with an optimal likelihood of accuracy (for example, by eliminating results that deviate from an approximate consensus, and/or averaging-based approaches).

Example Instrumented Mouthguard

FIG. 1A to FIG. 1D illustrate an instrumented mouthguard device according to one embodiment. This example instrumented mouthguard is configurable to operate as a HID device as discussed herein, to provide both impact detection functionality and physical performance functionality.

The mouthguard comprises a mouthguard inner body 100, an instrumented component 101, and an outer mouthguard body 160. In the present embodiment the mouthguard inner body is custom formed based for a user based on a dentition scanning process, such that the mouthguard inner body provides a customized specifically to that user. The instrumented component 101 is then affixed to the inner body, and the outer body 160 sealed to the inner body 100 thereby to sandwich the instrumented component.

Additional detail regarding example instrumented mouthguard construction processes are provided in Australian provisional patent application 2020904214, entitled "multi-layered instrumented mouthguard devices, and methods for manufacturing of instrumented mouthguard devices." The disclosure of that application is hereby incorporated by cross reference.

Instrumented component 101 includes a plurality of component zones 110, 120 and 130, which are spaced apart on a flexible PCB which follows a meandering path (i.e., the distance between component zones along the PCB is greater than the direct distance between the component zones).

The meandering path allows for mounting of the flexible circuit board substrate to the mouthguard inner body, such that the component zones are located in a frontal region of the mouthguard body (component zone 120); a side region of the mouthguard inner body (component zone 110); and an opposite side region of the mouthguard inner body from the second component zone (component zone 130). The frontal region is located on an opposite side of a teeth-receiving protective channel to the side region and opposite side region. In this example the frontal region is located on an inner side of the body relative to the protective channel, and the side region and opposite side regions are located on an outer side of the body relative to the protective channel. Outer body member cover 160 is mounted to the body thereby to seal components mounted on both the outer side of the inner body relative to the protective channel thereby to cover and the inner side of the inner body relative to the protective channel.

Figure 2A:
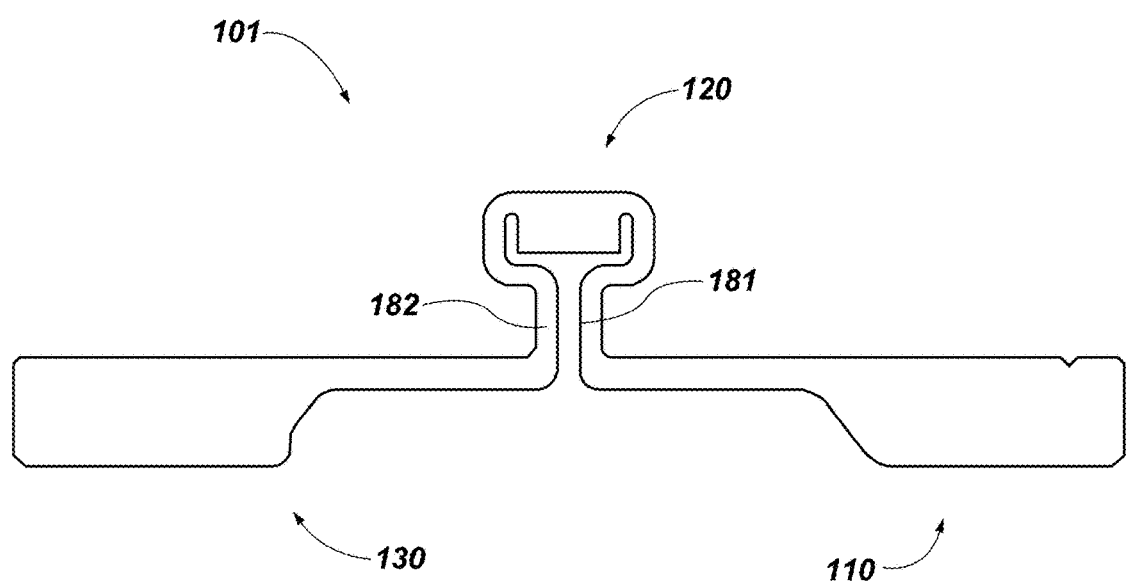
FIGS. 2A and 2B illustrate an example PCB component for an instrumented mouthguard.
Figure 2B:
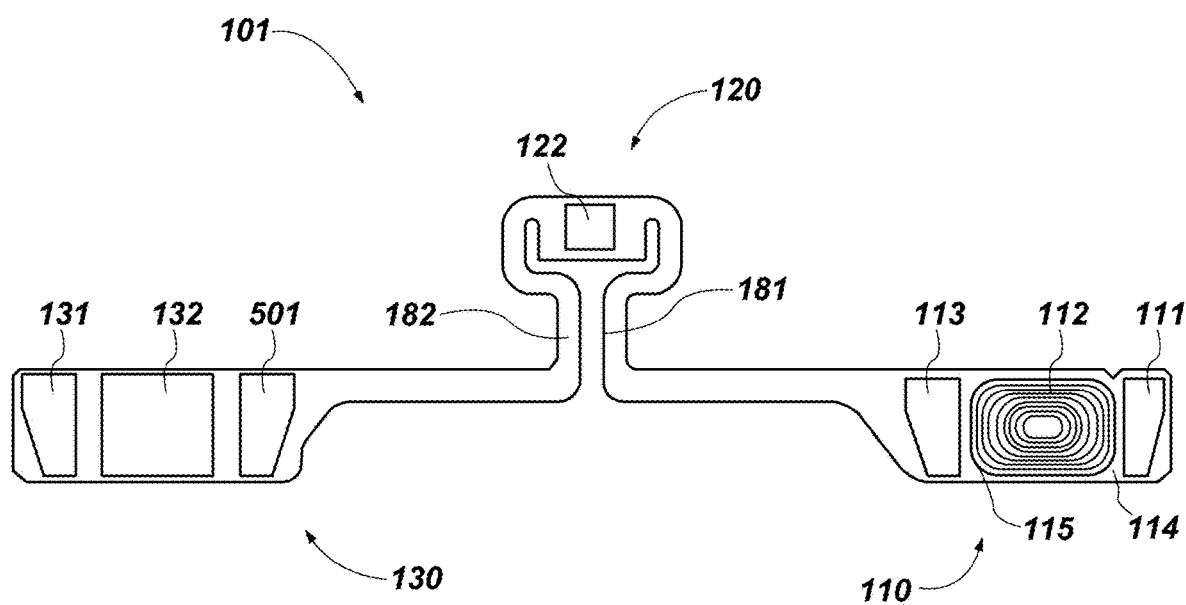

FIG. 2A and FIG. 2B illustrates an instrumented component 101 according to a further embodiment, this being configured for mounting in a mouthguard body thereby to provide an instrumented mouthguard.

As shown in FIG. 2A, component 101 is defined by a flexible circuit board substrate which is configured such that one or more conductive members electronically couples component zones (e.g., printed circuit board regions). The flexible circuit board in this manner defines a conductive member which is irregularly shaped such that it is configured to enable fitting of the component zones at desired locations on mouthguard bodies of varied shapes and sizes. More particularly, a PCB is formed to meander between component zones in a manner that allows for customizable fitting, while providing for added flexibility and robustness when the mouthguard is used. This presents a significant advantage over non-meandering PCBs, or the use of wires interconnecting distinct PCBs.

The PCB substrate illustrated in FIG. 2A may be of variable thickness, and/or have rigidity supports applied, thereby to adjust rigidity on a special basis thereby to protect PCB components as required for robustness.

Component 101 includes three component zones:
A right side component zone 110. In some implementations the right side component zone is configured to support PCB components including an accelerometer (3-axis), wireless communications unit, memory and microprocessor.
A frontal component zone 120. In some implementations, component zone 120 is split provides an accelerometer supporting zone configured to be positioned on the outer side of the front teeth (for a 3-axis accelerometer). In some embodiments, the frontal zone additionally includes a low-G accelerometer and/or a gyroscope.
A left side component zone 130. In some implementations the left side component zone provides mounting locations for an accelerometer (3-axis), battery charging unit, and a battery mounting location.

The positioning of components described above, and shown in FIG. 2B, is an example only, and in other embodiments, alternate configurations of components are distributed between the component zones.

A flexible connector member, defined by part of the PCB substrate onto which conductors connects these zones, has a first segment 181 which electronically couples right side component zone 110 and frontal component zone 120, and a second segment 182 which electronically couples front component zone 120 and left side component zone 130. As shown in FIGS. 2A and 2B, these segments are meandering. In this example, as with examples above, the meandering is such that, segment 181 is greater than the length of the separation of connection points with zones 110 and 120, and segment 182 is greater than the separation of connection points with zones 120 and 130.

The flexible connector member provides a flexible substrate onto which conductive strips and a plurality of PCB components are mounted (for example, PCB components in zones 110, 120 and 130). In some embodiments, the flexible substrate has an increased thickness in certain regions thereby to provide increased rigidity for PCB components that are susceptible to damage as a result of PCB flexion (for example, see regions 111, 112 and 113 discussed below). In some embodiments, additional materials are applied to the flexible substrate thereby to increase rigidity where required.

In the embodiment of FIG. 2B, zone 110 is defined by three substantially rigid PCB regions 111, 112 and 113, interconnected by comparatively flexible regions (flex connectors) 114 and 115. This enables a better fit of zone 110 to a curved surface; in the present embodiment it is configured to be mounted in a right cheek region of the mouthguard body. Zone 110 includes a range of electronic components, including:
A 3-axis accelerometer.
A microprocessor (for example, a Qualcomm CSR1012).
A memory module (for example, a Macronix MX25L3233).
A wireless communications module, in this embodiment being a Bluetooth module coupled to a Bluetooth antenna (not shown), for example, an antenna configured to be mounted such that it runs across a frontal region of the mouthguard forward of a wearer's teeth.
A coupling port to a programming tab (not shown).
A Light-Emitting Diode configured to be visible through the mouthguard body (not shown), in order to provide a device state indication to a user. For example, this is configured to be positioned behind the wearer's top lip.

It should be appreciated that the variations in rigidity within zone 110 (and across the component generally) is selected based at least in part of PCB components that are to be mounted at the various locations. For example, in one embodiment one or more of regions 111, 112 and 113 is not rigid, thereby to allow improved curvature upon application to the mouthguard body, and PCB components mounted to the non-rigid region are selected and/or mounted in such a manner to remain robust in spite to flexion in the PCB substrate.

Zone 120 includes a PCB region 122 including a 3-axis accelerometer (which is configured to be mounted to the mouthguard body in a location that in use is positioned behind front teeth). In the present embodiment PCB region 122 additionally includes a gyroscope, and a second accelerometer which is configured for lower levels of acceleration. Specifically, each component zone includes a 3-axis high-G accelerometer, and one component zone additionally includes a low-G accelerometer.

Zone 130 is configured to be mounted on a left cheek region of the mouthguard body, and includes a PCB that carries a 3-axis accelerometer 131, along with a charging coil 132 to enable wireless charging of a battery unit 151.

In other implementations the battery unit is located in zone 110 or zone 120. In further embodiments, additional components including the likes of gyroscopes may also be present at one or more of the component zones (for example, a gyroscope in combination with an accelerometer at each component zone).

Segment 181 of the conductive member is configured such that, upon mounting to the mouthguard body, it traverses across a bottom region of the mouthguard body at a region approximately adjacent cuspid and first bicuspid (or, alternately, first and second teeth). This allows zone 120 to be provided on an internal region (behind teeth) and zone 110 provided on an external region (in front of teeth). A sealing cover is mounted to the body thereby to seal components mounted on both the outer side of the body relative to the protective channel thereby to cover and the inner side of the body relative to the protective channel.

In a further embodiment, component 101 or a variant thereof is embedded into a post-manufacture customized (e.g., a "boil and bite") mouthguard. In such an embodiment, a standard generic form is injection molded, and a user heats the mouthguard into a temporarily deformable state and bites firmly into it thereby to shape the resilient materials substantially to their teeth before it cools and becomes stable in the new customized shape.

Example Technology Framework

Figure 3:
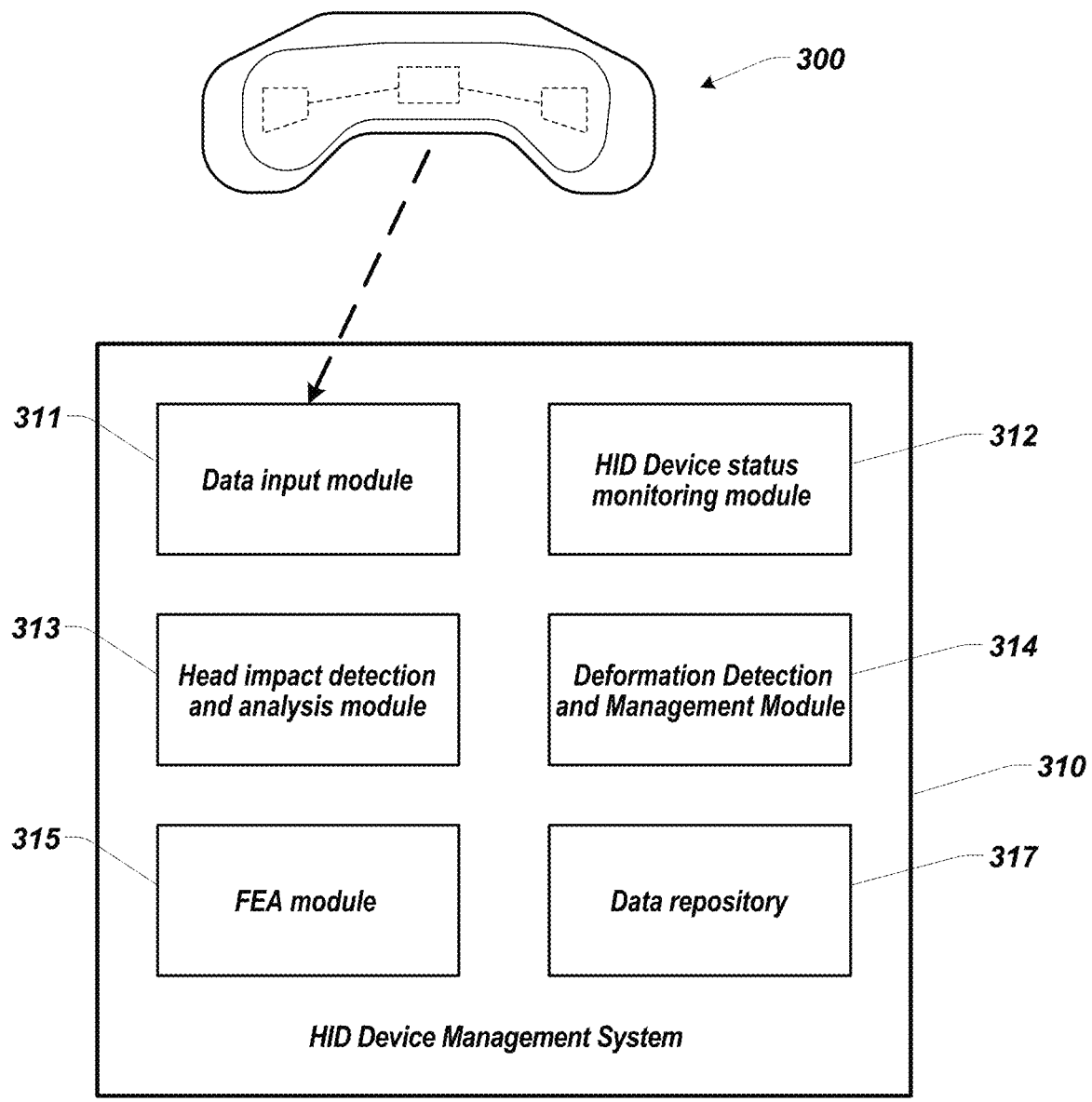
FIG. 3 illustrates a technology framework according to one embodiment.

FIG. 3 illustrates an example technology framework, configured to enable monitoring of head impacts and physical performance for one or more subjects in a sporting activity.

The framework is described by reference to a head impact detection (HID) device, in the form of an instrumented mouthguard 300, and an HID Device Management System 310, which takes the form of a computing device (for example, a PC, notebook, tablet or smartphone) or a plurality of computing devices (for example, various processing functionalities may be performed by cloud-hosted components). Instrumented mouthguard 300 includes a microprocessor configured to execute onboard software instructions, and it will be appreciated that various functions described as being performed by system 310 may in further embodiments, be performed in whole or in part by mouthguard 300.

Software is described herein by reference to various modules. The term "module" refers to a software component that is logically separable (a computer program), or a hardware component. The module of the embodiment refers to not only a module in the computer program but also a module in a hardware configuration. The discussion of the embodiment also serves as the discussion of computer programs for causing the modules to function (including a program that causes a computer to execute each step, a program that causes the computer to function as means, and a program that causes the computer to implement each function), and as the discussion of a system and a method. For convenience of explanation, the phrases "stores information," "causes information to be stored," and other phrases equivalent thereto are used. If the embodiment is a computer program, these phrases are intended to express "causes a memory device to store information" or "controls a memory device to cause the memory device to store information." The modules may correspond to the functions in a one-to-one correspondence. In a software implementation, one module may form one program or multiple modules may form one program. One module may form multiple programs. Multiple modules may be executed by a single computer. A single module may be executed by multiple computers in a distributed environment or a parallel environment. One module may include another module. In the discussion that follows, the term "connection" refers to not only a physical connection but also a logical connection (such as an exchange of data, instructions, and data reference relationship). The term "predetermined" means that something is decided in advance of a process of interest. The term "predetermined" is thus intended to refer to something that is decided in advance of a process of interest in the embodiment. Even after a process in the embodiment has started, the term "predetermined" refers to something that is decided in advance of a process of interest depending on a condition or a status of the embodiment at the present point of time or depending on a condition or status heretofore continuing down to the present point of time. If "predetermined values" are plural, the predetermined values may be different from each other, or two or more of the predetermined values (including all the values) may be equal to each other. A statement that "if A, B is to be performed" is intended to mean "that it is determined whether something is A, and that if something is determined as A, an action B is to be carried out." The statement becomes meaningless if the determination as to whether something is A is not performed.

The term "system" refers to an arrangement where multiple computers, hardware configurations, and devices are interconnected via a communication network (including a one-to-one communication connection). The term "system," and the term "device," also refer to an arrangement that includes a single computer, a hardware configuration, and a device. The system does not include a social system that is a social "arrangement" formulated by humans.

At each process performed by a module, or at one of the processes performed by a module, information as a process target is read from a memory device, the information is then processed, and the process results are written onto the memory device. A description related to the reading of the information from the memory device prior to the process and the writing of the processed information onto the memory device subsequent to the process may be omitted as appropriate. The memory devices may include a hard disk, a random-access memory (RAM), an external storage medium, a memory device connected via a communication network, and a ledger within a CPU (Central Processing Unit).

In the example of FIG. 3, instrumented mouthguard 300 communicates with system 310 via a wireless connection. This may include a range of wireless technologies, including WiFi, Bluetooth, and/or other radio bands. In some embodiments, communications between mouthguard 300 and system 310 progresses via one or more intermediate devices, including on-body retransmitting devices, devices in mesh networks, routers, and so on.

Data transmitted by mouthguard 300 is received by a data input module 311. Data input module 311 is configured to extract and sort input data, thereby to organize that data into memory accessible to system 310 (for example, in one or more databases). This includes identifying a unique device identifier associated with mouthguard 300, which is preferably associated with a unique human subject. The data may include, for example, any one or more of: (i) a time-series of sensor readings, with associated time correlation data (such as a timestamp at the commencement of the series, and a known sampling rate); (ii) data packets representative of identified potential impact events (for example, where the mouthguard is configured to operate in at least one setting where it transmits sensor data only where that sensor data has threshold values which indicate a potential impact); and (iii) output data from an onboard processing module (for example, on onboard FEA module which provides an output based on a dosage input, the dosage input being derived from sensor data); and (iv) regular beacon/heartbeat data packets representative of device status. Other data may also be received, for example, physiological data (such as heart rate, breathing rate, etc.).

Data received and processed via input module 311 is stored in a data repository 317, where it is available for accessing and processing by other modules of system 310.

A HID device status monitoring module 312 is configured to process data received via input module 311 thereby to determine a current status of mouthguard 300 and optionally one or more further mouthguard devices. This may be used to assess whether one or more mouthguards are in a fault state or the like. In some embodiments, module 312 is configured to enable two-way communication with mouthguard 300, for example, to enable remote switching of mouthguard 300 between multiple distinct operational settings (for example, one optimized for impact detection, and one optimized for physical performance assessment).

A head impact detection and analysis module 313 is configured to process data derived from sensors of mouthguard 300 thereby to provide metrics representative of severity of an observed impact event. It will be appreciated that there are a range of technologies which may be used for this processing, for example, using techniques to process linear and/or rotational acceleration, optionally using AI methods and/or benchmarking against existing data. In this example, module 313 operates in conjunction with a Finite Element Analysis (FEA) module 315. Module 313 is configured to process sensor data thereby to define a dosage input signal. This may include processing time correlated data from multiple sensors thereby to determine an acceleration value at a defined location (for example, at the center of gravity of the subject's head, preferably based on transforms which are individually customized for the particular human subject based on their mouthguard and physical head configuration). This acceleration value is passed to FEA module 315, which performs analysis thereby to provide one or more metrics representative of predicted effect of the acceleration to the subject's brain (impact parameters), thereby to provide data which assists in understanding anticipated severity of a head impact.

A deformation detection and management module 314 operates in conjunction with module 313 thereby to provide improved processing of is configured motion sensor component data thereby to derive better accuracy impact parameters. This module is configured to reduce the effect of data inconsistencies resulting from mouthguard deformation. This may include either or both of the following:

- Where a given one of the motion sensor components provides data which is inconsistent with a rigid body assumption to which others of the motion sensor components conform, excluding that given one of the motion sensor components from consideration when calculating the impact parameters.
- Where there is greater than threshold inconsistency between values from spaced apart motion senor components, determining that associated data describes an out-of-mouth event as opposed to a head impact.

Example processes performed by modules 313 and 314, thereby to determine impact parameters from motion sensor data in a manner which accounts for effects of mouthguard body deformation, are discussed in more detail below.

Accounting for Local Deformation During Impact Events

As noted, in some embodiments, a step of determining impact parameters for the impact event, is performed in a manner which accounts for local deformation of the mouthguard body. This is particularly relevant where a head impact has resulted from a facial strike in the vicinity of a component zone of the instrumented mouthguard device. For example, in the context of boxing, this may be a punch received to the front or side of the face. Such an impact has the potential to deform the mouthguard body in the area of a given motion sensor component, causing that motion sensor component to record a localized acceleration reading which is different to that registered at others of the motion sensor components. The motion sensor component which is affected by the localized strike provides data which is inaccurate in terms of the acceleration of the center of gravity of the subject's head (by comparison to data from other sensors which were not affected by the localized strike).

Local deformation may also be a result of an out-of-mouth event, being an impact event in which the mouthguard's deformable body is not maintained in a substantially rigid form by the subject's jaw (for example, the mouthguard is dropped, carried in a pocket, and so on).

Preferred embodiments apply methods whereby determination of impact parameters for an impact event is based on processing of data from a subset of the motion sensor components. This subset of the motion sensor components excludes one (or more) of the motion sensor components determined to have been affected by local deformation of the mouthguard body. This may include either or both of:

- Selection of a subset of data from the motion sensor components, and then performing a process for determination of impact parameters from those. For example, this selection process may include comparing data from three spaced apart accelerometers (which in a perfect rigid body should each have threshold conformance, for example, when translated to the center of mass of the head), and applying a voting system such that the two accelerometers with best conformity are used, and the other omitted. In the case that there is insufficient conformity between any pair of the accelerometers, the impact may be categorized as a predicted out-of-mouth (or otherwise unreliable) event.
- Performing a plurality of process for determination of impact parameters from distinct combinations of subset of data from the motion sensor components, and excluding one or more outcomes based on deviations from a consensus range defined by a majority of outcomes. In the event that there is insufficient consensus across the outcomes, the impact may be categorized as a predicted out-of-mouth (or otherwise unreliable) event.

Some examples are provided below. For these examples, it is assumed that the instrumented mouthguard device has three component zones, each having a respective three-axis accelerometer, with at least one of the component zones including a gyroscope. In further embodiments, either the gyroscope or one of the accelerometers might be omitted.

Figure 4A:
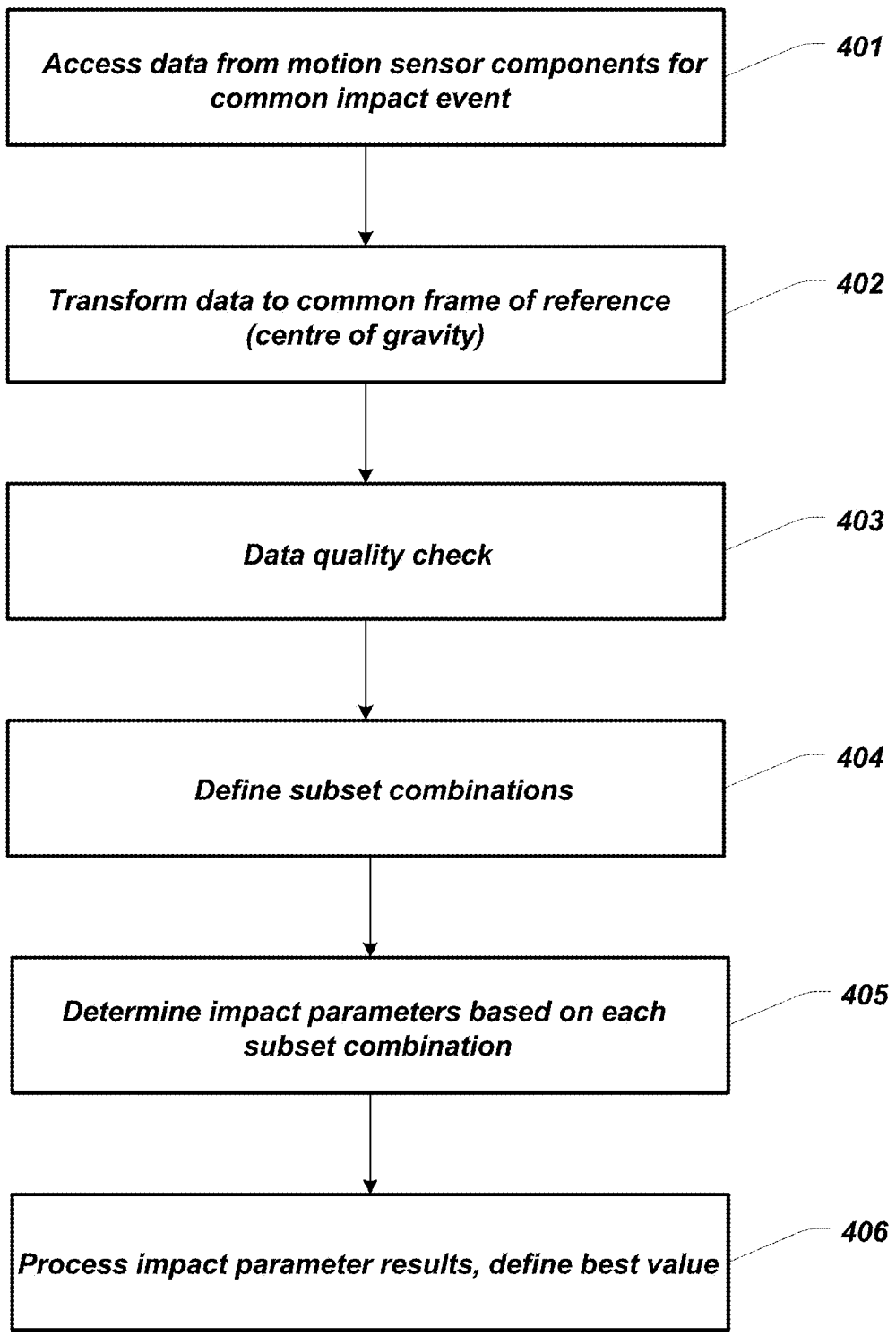
FIG. 4A and FIG. 4B illustrate example methods according to embodiments.

A first example is shown in FIG. 4A. In this example, sensor data for an impact event is accessed at block 401. This data is defined by a set of time correlated samples (for example, acceleration data samples) for each of the motion sensor components. Block 402 represents a process including transforming the sensor data from each sensor to a common frame of reference, in this case being the center of gravity of the subject's head. For example, this is performed based on transforms defined during an individualized calibration process specific to a unique combination of a mouthguard and a user (taking into consideration positions of sensors within the mouthguard body, and the position of the mouthguard body relative to the center of gravity of the subject's brain), such as a method disclosed in Australian Provisional Patent Application 2020900733, which is herein incorporated by cross reference. In some embodiments, the process of block 402 is performed at an earlier stage, including via on-board processing on the mouthguard device prior to step 401.

Step 403 represents a data integrity check. This is optionally performed thereby to ensure that the data from the motion sensor components meets threshold requirements, for example, in terms of consistency or data reliability. If these requirements are not met, the impact event may be flagged as "unreliable" or the like, or in some cases data from one motion sensor component is discarded. This step may also be performed earlier in the process.

Step 404 represents defining of subset combinations. This includes defining unique subsets of the motion sensor components which will be used for each of a plurality of impact parameter determination processes. In this example, there are 3 accelerometers and one gyroscope. It will be appreciated that impact parameters may be calculated using any of the following combinations:

- Two accelerometers and one gyroscope.
- Three accelerometers (no gyroscope).
- Three accelerometers and one gyroscope.
- Two accelerometers and no gyroscope (for example, via a particle filter method).

Step 405 represents determining impact parameters based on each subset combination. This yields a plurality of impact parameter results (or failed results, for example, where a model is unable to complete a calculation, for example, due to failure of a data set to conform with a rigid body assumption for a rigid body kinematic model).

Step 406 then represents processing the results, thereby to define a "best" value. This "best" value may be determined via a number of techniques, for example, including one or more of the following:

Identifying results which are within a threshold range of one another, and excluding other results.
   Of the results which are within a threshold range of one another, selecting one from a processing model deemed most reliable.
   Using the results which are within a threshold range of one another, performing an averaging technique (which may be a weighted averaging technique, in which processing models deemed relatively more reliable are given relatively greater weighting).

It will be appreciated that such a technique is effective in accounting for the impact of deformation of the instrumented mouthguard as a result of a localized impact (and/or sensor faults), when determining impact parameters for the center of gravity for the subject's head. In particular, by running a plurality of calculations of impact parameters based on different sets of sensor data combinations, the technology is configured to enable determination of a "consensus" result which omits data from one or more sensors which may be affected by local mouthguard deformation, or faulty for other reasons.

Figure 4B:
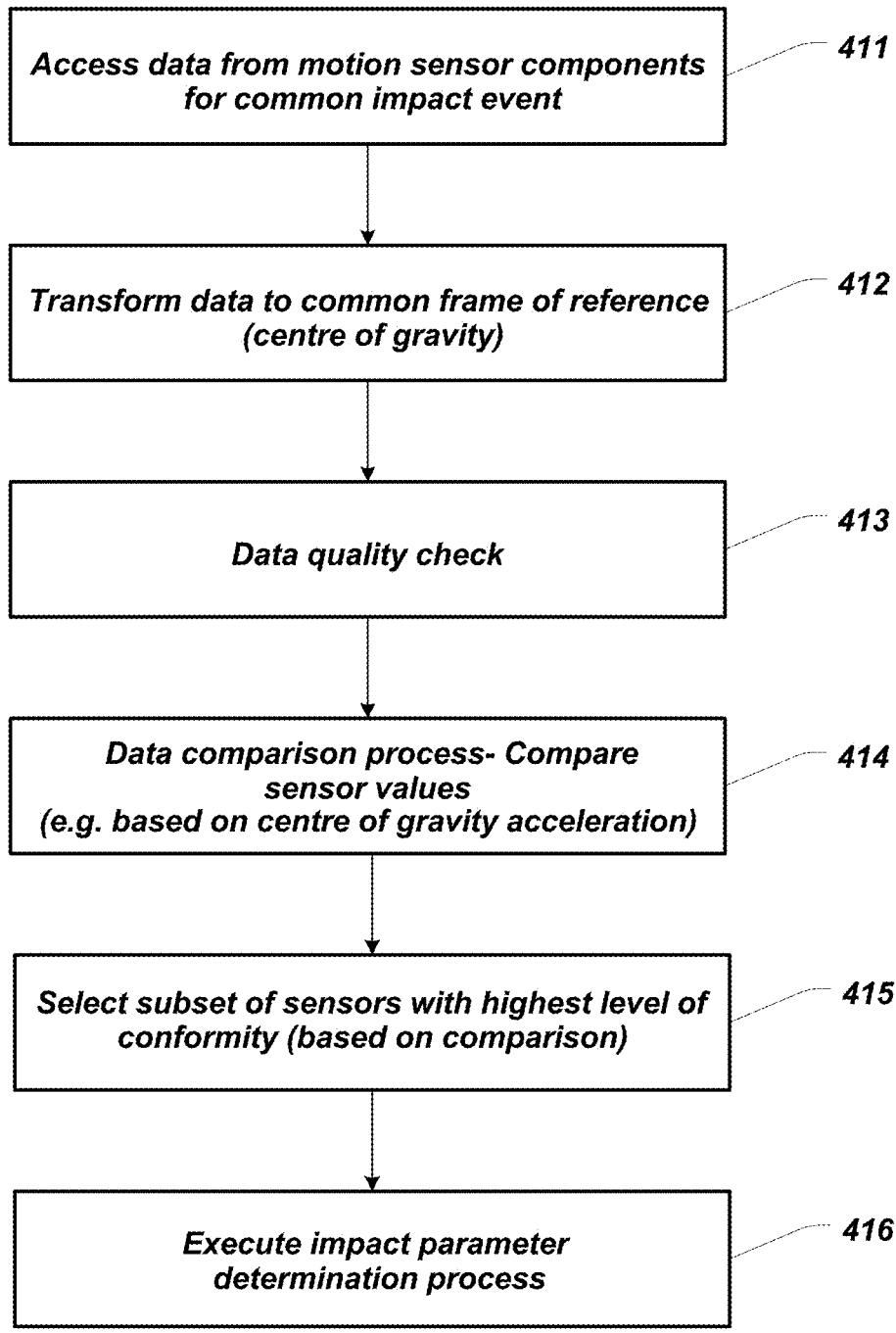

A second example is shown in FIG. 4B. In this example, sensor data for an impact event is accessed at block 411. This data is defined by a set of time correlated samples (for example, acceleration data samples) for each of the motion sensor components. Block 412 represents a process including transforming the sensor data from each sensor to a common frame of reference, in this case being the center of gravity of the subjects head. For example, this is performed based on transforms defined during an individualized calibration process specific to a unique combination of a mouthguard and a user (taking into consideration positions of sensors within the mouthguard body, and the position of the mouthguard body relative to the center of gravity of the subject's brain), such as a method disclosed in Australian Provisional Patent Application 2020900733, which is herein incorporated by cross reference. In some embodiments, the process of block 412 is performed at an earlier stage, including via on-board processing on the mouthguard device prior to step 411.

Step 413 represents a data integrity check. This is optionally performed thereby to ensure that the data from the motion sensor components meets threshold requirements, for example, in terms of consistency or data reliability. If these requirements are not met, the impact event may be flagged as "unreliable" or the like, or in some cases data from one motion sensor component is discarded. This step may also be performed earlier in the process.

Step 414 represents a data comparison process, whereby sensor-measured values (e.g., acceleration values, such as acceleration values transformed to the center of gravity) from each of the sensors are compared, thereby to determine: (i) a first group of sensors for which acceleration values are within a threshold level of conformity; and (ii) a second group of one or more sensors for which acceleration values are outside that threshold level of conformity with the first group. The second group may in many cases be defined by a single accelerometer. The first group of sensors is selected at 415 for impact parameter determination, on the basis that these best conform to a rigid body assumption used for a rigid body kinematics based calculation of impact parameters at the center of gravity of the subject's head. An impact parameter determination process is then performed at 416.

In this example, it is assumed that the processing logic used for impact parameter determination relies on having at least N inputs (where N is an integer$\geq 1$) and that the one or more motion sensor components from each of the component zones provide a total of N+X motion sensor components, and X is an integer$\geq 1$. For example, where there are three 3-axis accelerometers and one gyroscope, N+X is 4. The process of block 415 includes selecting a subset of N+Y of the motion sensor components, where Y is an integer$\geq 0$, wherein the data derived from that subset of the motion sensor components is used by the selected rigid body kinematic model thereby to determine a best value for the acceleration value at a defined point on the subject's head.

Again, it will be appreciated that such a technique is effective in accounting for the impact of deformation of the instrumented mouthguard as a result of a localized impact (and/or sensor faults), when determining impact parameters for the center of gravity for the subject's head. In particular, by running a plurality of calculations of impact parameters based on different sets of sensor data combinations, the technology is configured to enable determination of a "consensus" result which omits data from one or more sensors which may be affected by local mouthguard deformation, or faulty for other reasons.

It will be appreciated that other methods may be used in the context of the same objective, being excluding data from one or more sensors from consideration in the ultimate determination of impact parameters. It will additionally be appreciated that the above techniques are able to, in addition to accounting for mouthguard deformations, allow for an instrumented mouthguard to function even if one of the accelerometers has been damaged (or is otherwise faulty).

Conclusions and Interpretation

The disclosure above provides improved technology for assessing head impacts via an instrumented mouthguard device. In particular, identifying and accounting for sensor data which may be affected by mouthguard deformation allows for both better accuracy in generation of impact parameter values, and an ability to identify our-of-mouth events.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements, if any, in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

Various aspects of the present disclosure may be embodied as a program, software, or computer instructions embodied in a computer or machine usable or readable medium, which causes the computer or machine to perform the steps of the method when executed on the computer, processor, and/or machine. A program storage device readable by a machine, tangibly embodying a program of instructions executable by the machine to perform various functionalities and methods described in the present disclosure is also provided.

A system and method of the present disclosure may be implemented and run on a general-purpose computer or special-purpose computer system. The terms "computer system" and "computer network" as may be used in the present application may include a variety of combinations of fixed and/or portable computer hardware, software, peripherals, and storage devices. The computer system may include a plurality of individual components that are networked or otherwise linked to perform collaboratively, or may include one or more stand-alone components. The hardware and software components of the computer system of the present application may include and may be included within fixed and portable devices such as desktop, laptop, and/or server. A module may be a component of a device, software, program, or system that implements some "functionality," which can be embodied as software, hardware, firmware, electronic circuitry, or etc.

Although specific embodiments of the present invention have been described, it will be understood by those of skill in the art that there are other embodiments that are equivalent to the described embodiments. Accordingly, it is to be understood that the invention is not to be limited by the specific illustrated embodiments, but only by the scope of the appended claims.

It should be appreciated that in the above description of exemplary embodiments of the invention, various features of the invention are sometimes grouped together in a single embodiment, FIG., or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those skilled in the art. For example, in the following claims, any of the claimed embodiments can be used in any combination.

Furthermore, some of the embodiments are described herein as a method or combination of elements of a method that can be implemented by a processor of a computer system or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the invention.

In the description provided herein, numerous specific details are set forth. However, it is understood that embodiments of the invention may be practiced without these specific details. In other instances, well-known methods, structures and techniques have not been shown in detail in order not to obscure an understanding of this description.

Similarly, it is to be noticed that the term coupled, when used in the claims, should not be interpreted as being limited to direct connections only. The terms "coupled" and "connected," along with their derivatives, may be used. It should be understood that these terms are not intended as synonyms for each other. Thus, the scope of the expression a device A coupled to a device B should not be limited to devices or systems wherein an output of device A is directly connected to an input of device B. It means that there exists a path between an output of A and an input of B, which may be a path including other devices or means. "Coupled" may mean that two or more elements are either in direct physical or electrical contact, or that two or more elements are not in direct contact with each other but yet still co-operate or interact with each other.

Thus, while there has been described what are believed to be the preferred embodiments of the invention, those skilled in the art will recognize that other and further modifications may be made thereto without departing from the spirit of the invention, and it is intended to claim all such changes and modifications as falling within the scope of the invention. For example, any formulas given above are merely representative of procedures that may be used. Functionality may be added or deleted from the block diagrams and operations may be interchanged among functional blocks. Steps may be added or deleted to methods described within the scope of the present invention.

What is claimed is:

1. A method for processing impact event data for an impact event, wherein the impact event data is derived from an instrumented mouthguard device, wherein the instrumented mouthguard device includes:
   a body formed of deformable materials, wherein the body is shaped to be worn by a subject as a mouthguard;
   a plurality of component zones embedded in the body, wherein the component zones are spaced apart, and wherein each component zone includes one or more motion sensor components;
   (i) predicting that the impact event data from a given one of the motion sensor components is potentially affected by local deformation of the mouthguard body; and
   (ii) determining impact parameters for the impact event which account for that local deformation of the mouthguard body.

2. A method according to claim 1, wherein determining impact parameters for the impact event which account for that local deformation of the mouthguard body includes:
   determining impact parameters for the impact event based on processing of data from a subset of the motion sensor components, wherein the subset of the motion sensor components excludes the given one of the motion sensor components determined to have been affected by local deformation of the mouthguard body.

3. A method according to claim 2, wherein determining that the impact event data from a given one of the motion sensor components is affected by local deformation of the mouthguard body includes determining that time correlated sensor data values from the given one of the motion sensor components does not conform to a rigid body assumption which is supported by others of the motion sensor components.

4. A method according to claim 1, wherein determining impact parameters for the impact event which account for that local deformation of the mouthguard body includes:
determining that the impact event is an out-of-mouth event.

5. A method according to claim 4 including determining that the impact is an out of mouth event in the case that there is threshold deviation from a rigid body assumption between time-correlated data from data from two or more of the component zones.

6. A method according to claim 4 including determining that the impact is an out of mouth event in the case that there is threshold disagreement between time-correlated data from data from two or more of the component zones when data is projected to a common location defined on the subject's head.

7. A method for processing data derived from an instrumented mouthguard device, wherein the instrumented mouthguard device includes:
a body formed of deformable materials, wherein the body is shaped to be worn by a subject as a mouthguard;
a plurality of motion sensor components embedded in the body at spaced apart locations;
the method including:
(i) accessing an impact data set (IDS) relating to a predicted impact event, wherein the impact data set includes, for each of the plurality of motion sensor components embedded in the body, a respective series of motion sensor component data samples corresponding to the predicted impact event;
(ii) processing the impact data set thereby to determine whether the respective series of samples each conform to a common rigid body assumption;
(iii) in the case that: a plurality of the series of samples conform to the common rigid body assumption; and one or more of the series of samples diverge from the common rigid body assumption, either:
(A) performing a head acceleration determination process for the predicted head impact event using the plurality of the samples that conform to the common rigid body assumption; or
(B) determining that the predicted head impact event is an out-of-mouth event.

8. A method according to claim 7, wherein the plurality of motion sensor components include: at least three 3-axis accelerometers.

9. A method according to claim 7, wherein the plurality of motion sensor components include: at least 3-axis accelerometers and a gyroscope.

10. A method according to claim 7, wherein the method includes performing a transformation process thereby to transform data from each of the motion sensor components to data at a predefined common location defined in the subject's head.

11. A method according to claim 10, wherein the predefined common location is an approximate center of gravity of the subject's head.

12. A method according to claim 7, the method is performed using calibration data which enable transformation of data from each of the motion sensor components to a predefined common location defined in the subject's head.

13. A method according to claim 12, wherein the calibration data is defined specifically for: locations of the motion sensor components in the body, which provides uniquely shaped fit for the subject.

14. A method according to claim 12, wherein the calibration data is defined specifically for: (i) locations of the motion sensor components in the body, which provides uniquely shaped fit for the subject; and (ii) fitting of that body in the subject's head, wherein the body is shaped individually for the subject.

15. A method for processing data derived from an instrumented mouthguard device, wherein the instrumented mouthguard device includes:
a body formed of deformable materials, wherein the body is shaped to be worn by a subject as a mouthguard;
at least two component zones embedded in the body, wherein the component zones are spaced apart, and wherein each component zone includes one or more motion sensor components;
the method including:
(i) selecting a rigid body kinematic model which is configured to determine an acceleration value at a defined point on the subject's head, wherein the model requires data points from N motion sensor components, where N is an integer$\geq 2$;
(ii) accessing data derived from the one or more motion sensor components from each of the component zones, wherein the data is time correlated and relates to a common potential impact event, wherein the one or more motion sensor components from each of the component zones provide a total of N+X motion sensor components, where X is an integer$\geq 1$;
(iii) performing a process thereby to select a subset of N+Y of the motion sensor components, where Y is an integer$\geq 0$, wherein the data derived from that subset of the motion sensor components is used by the selected rigid body kinematic model thereby to determine a best value for the acceleration value at a defined point on the subject's head.

16. A method according to claim 15, wherein the plurality of motion sensor components include: at least three 3-axis accelerometers.

17. A method according to claim 15, wherein the plurality of motion sensor components include: at least 3-axis accelerometers and a gyroscope.

18. A method according to claim 15, wherein the method includes performing a transformation process thereby to transform data from each of the motion sensor components to data at a predefined common location defined in the subject's head.

19. A method according to claim 18, wherein the predefined common location is an approximate center of gravity of the subject's head.

20. A method according to claim 15, wherein the method is performed using calibration data which enable transformation of data from each of the motion sensor components to a predefined common location defined in the subject's head.

21. A method according to claim 20, wherein the calibration data is defined specifically for: locations of the motion sensor components in the body, which provides uniquely shaped fit for the subject.

22. A method according to claim 20, wherein the calibration data is defined specifically for: (i) locations of the motion sensor components in the body, which provides uniquely shaped fit for the subject; and (ii) fitting of that body in the subject's head, wherein the body is shaped individually for the subject.

23. A method for processing data derived from an instrumented mouthguard device, wherein the instrumented mouthguard device includes:
   a body formed of deformable materials, wherein the body is shaped to be worn by a subject as a mouthguard;
   at least two component zones embedded in the body, wherein the component zones are spaced apart, and wherein each component zone includes one or more motion sensor components;
   the method including:
      (i) accessing data derived from the one or more motion sensor components from each of the component zones, wherein the data is time correlated and relates to a common potential impact event, wherein the one or more motion sensor components from each of the component zones provide a total of N+X motion sensor components, where N is an integer≥2 and X is an integer≥1;
      (ii) executing a plurality of models thereby to determine respective acceleration metric for the potential impact event at a predefined location on the subject's head, wherein each model requires data from N+Y of the motion sensor components, where Y is an integer≥0, wherein solved using a unique combination of the motion sensor components;
      (iii) performing a process configured to derive a best acceleration metric from the respective acceleration metrics determined from the plurality of models.

24. A method according to claim 23, wherein the process configured to derive a best acceleration metric from the determined acceleration metrics determined from the plurality of models includes: omitting one or more of the determined acceleration metrics determined from the plurality of models where that one or more of the determined acceleration metrics have a threshold deviation from the remaining determined acceleration metrics.

25. A method according to claim 23, wherein the process configured to derive a best acceleration metric from the determined acceleration metrics determined from the plurality of models includes: identifying a subset of the determined acceleration metrics that are within a threshold range of each other, and deriving the best acceleration metric from that subset.

26. A method according to claim 25, wherein deriving the best acceleration metric from that subset includes an averaging process.

27. A method according to claim 19, wherein deriving the best acceleration metric from that subset includes a selection process.

28. A method according to claim 23, wherein the plurality of motion sensor components include: at least three 3-axis accelerometers.

29. A method according to claim 23, wherein the plurality of motion sensor components include: at least 3-axis accelerometers and a gyroscope.

30. A method according to claim 23, wherein the method includes performing a transformation process thereby to transform data from each of the motion sensor components to data at a predefined common location defined in the subject's head.

31. A method according to claim 30, wherein the predefined common location is an approximate center of gravity of the subject's head.

32. A method according claim 23, wherein the method is performed using calibration data which enable transformation of data from each of the motion sensor components to a predefined common location defined in the subject's head.

33. A method according to claim 32, wherein the calibration data is defined specifically for: locations of the motion sensor components in the body, which provides uniquely shaped fit for the subject.

34. A method according to claim 32, wherein the calibration data is defined specifically for: (i) locations of the motion sensor components in the body, which provides uniquely shaped fit for the subject; and (ii) fitting of that body in the subject's head, wherein the body is shaped individually for the subject.

35. A method for processing impact event data for an impact event, wherein the impact event data is derived from an instrumented mouthguard device, wherein the instrumented mouthguard device includes:
   a body formed of deformable materials, wherein the body is shaped to be worn by a subject as a mouthguard; and
   a plurality of spaced apart accelerometers;
   the method including:
      (i) processing data from the plurality of spaced apart accelerometers;
      (ii) identifying a subset of the spaced part accelerometers which have threshold conformity on acceleration parameters for a common impact event;
      (ii) determining impact parameters for the impact event based on that subset of the spaced apart accelerometers.

36. A method for processing impact event data for an impact event, wherein the impact event data is derived from an instrumented mouthguard device, wherein the instrumented mouthguard device includes:
   a body formed of deformable materials, wherein the body is shaped to be worn by a subject as a mouthguard; and
   motion sensing components including a plurality of spaced apart accelerometers and at least one gyroscope;
   the method including: determining a measurement of acceleration at a specified location on the subject's head using a subset of the motion sensing components, thereby to account for localized deformation of the body proximal a given one of the motion sensing components.

37. A method for processing impact event data for an impact event, wherein the impact event data is derived from an instrumented mouthguard device, wherein the instrumented mouthguard device includes:
   a body formed of deformable materials, wherein the body is shaped to be worn by a subject as a mouthguard; and
   motion sensing components including at least three spaced apart accelerometers and at least one gyroscope;
   the method including:
      (i) determining a proxy gyroscope value using the at least three accelerometers;
      (ii) comparing the proxy gyroscope value with the value from the at least one gyroscope.

38. A method according to claim 37 additionally including applying a decision process thereby to decide between using the proxy gyroscope value or the value from the at least one gyroscope for the purpose of determining a best prediction for acceleration of the subject's head.

* * * * *